US00PP37831P2

(12) United States Plant Patent
Barends

(10) Patent No.: US PP37,831 P2
(45) Date of Patent: Oct. 27, 2026

(54) ***BEGONIA* PLANT NAMED 'Dobegmotwohopi 33'**

(50) Latin Name: ***Begonia* x *hiemalis***
Varietal Denomination: Dobegmotwohopi 33

(71) Applicant: DUMMEN GROUP B.V., De Lier (NL)

(72) Inventor: Eveline Barends, De Lier (NL)

(73) Assignee: Dammen Group B.V., De Lier (NL)

( * ) Notice: Subject to any disclaimer, the term of this patent is extended or adjusted under 35 U.S.C. 154(b) by 0 days.

(21) Appl. No.: 19/648,654

(22) Filed: Apr. 15, 2026

(51) Int. Cl.
*A01H 5/02* (2018.01)

(52) U.S. Cl.
USPC ..... Plt./349

(58) Field of Classification Search
USPC ..... Plt./263.1, 343, 344, 349
See application file for complete search history.

(56) References Cited

U.S. PATENT DOCUMENTS

PP36,445 P2 * 2/2025 Mousa ..... A01H 6/185
Plt./349

* cited by examiner

*Primary Examiner* — Karen M Redden
(74) *Attorney, Agent, or Firm* — C. Anne Whealy

(57) ABSTRACT

A new and distinct cultivar of *Begonia* plant named 'Dobegmotwohopi 33', characterized by its compact, upright and uniformly mounded plant habit; vigorous growth habit; freely branching habit; dark green-colored leaves; freely and continuously flowering habit; and double-type flowers with petals that are bright purplish red in color.

1 Drawing Sheet

Botanical designation: *Begonia* x *hiemalis*.
Cultivar denomination: 'DOBEGMOTWOHOPI 33'.

BACKGROUND OF THE INVENTION

The present invention relates to a new and distinct cultivar of *Begonia* plant, botanically known as *Begonia* x *hiemalis*, commonly referred to as a Elatior *Begonia* and hereinafter referred to by the name 'Dobegmotwohopi 33'.

The new *Begonia* plant is a product of a planned breeding program conducted by the Inventor in De Lier, The Netherlands. The objective of the breeding program was to develop new freely flowering *Begonia* plants with upright plant habit, vigorous growth habit and double type flowers.

The new *Begonia* plant originated from a cross-pollination made by the Inventor in October, 2019 of a proprietary breeding selection of *Begonia* x *hiemalis* identified as code number BG15-000801-003, not patented, as the female, or seed, parent with a proprietary breeding selection of *Begonia* x *hiemalis* identified as code number BG1463, not patented, as the male or pollen, parent. The new *Begonia* plant was discovered and selected by the Inventor as a single flowering plant from within the progeny of the stated cross-pollination in a controlled greenhouse environment in De Lier, The Netherlands in May, 2020.

Asexual reproduction of the new *Begonia* plant by vegetative tip cuttings in a controlled greenhouse environment in De Lier, The Netherlands since June, 2020 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Dobegmotwohopi 33'. These characteristics in combination distinguish 'Dobegmotwohopi 33' as a new and distinct *Begonia* plant:

1. Compact, upright and uniformly mounded plant habit.
2. Vigorous growth habit.
3. Freely branching habit.
4. Dark green-colored leaves.
5. Freely and continuously flowering habit.
6. Double-type flowers with petals that are bright purplish red in color.

Plants of the new *Begonia* can be compared to plants of the female parent selection. In side-by-side comparisons, plants of the new *Begonia* differ primarily from plants of the female parent selection in flower color as flower petals of plants of the new *Begonia* are bright purplish red in color whereas flower petals of plants of the female parent selection are dark salmon in color. In addition, leaves of plants of the new *Begonia* are dark green in color whereas leaves of plants of the female parent selection are brown in color.

Plants of the new *Begonia* can be compared to plants of the male parent selection. In side-by-side comparisons, plants of the new *Begonia* differ primarily from plants of the male parent selection in flower color as flower petals of plants of the new *Begonia* are bright purplish red in color whereas flower petals of plants of the male parent selection are light salmon in color. Flowers of plants of the new *Begonia* are larger than flowers of plants of the male parent selection. In addition, leaves of plants of the new *Begonia* are dark green in color whereas leaves of plants of the male parent selection are light green in color Plants of the new *Begonia* can be compared to plants of *Begonia* x *hiemalis* 'Dobegmotwohopi', disclosed in U.S. Plant Pat. No. 36,445. In side-by-side comparisons, plants of the new *Begonia* differ primarily from plants of 'Dobegmotwohopi' in the following characteristics:

1. Plants of the new *Begonia* are more compact than plants of 'Dobegmotwohopi'.
2. Plants of the new *Begonia* have larger leaves than plants of 'Dobegmotwohopi'.
3. Leaves of plants of the new *Begonia* are slightly lighter in color than leaves of plants of 'Dobegmotwohopi'.
4. Plants of the new *Begonia* have larger flowers than plants of 'Dobegmotwohopi'.
5. Flowers of plants of the new *Begonia* have more petaloids than flowers of plants of 'Dobegmotwohopi'.
6. Flower petals of plants of the new *Begonia* are bright purplish red in color whereas flower petals of plants of 'Dobegmotwohopi' are vivid purplish pink in color.

BRIEF DESCRIPTION OF THE PHOTOGRAPH

The accompanying colored photograph illustrates the overall appearance of the new *Begonia* plant showing the colors as true as it is reasonably possible to obtain in colored reproductions of this type. Colors in the photograph may differ slightly from the color values cited in the detailed botanical description which accurately describe the colors of the new *Begonia* plant.

The photograph is a side perspective view of a typical flowering plant of 'Dobegmotwohopi 33' grown in a container.

DETAILED BOTANICAL DESCRIPTION

Plants used for the aforementioned photograph and following observations and measurements were grown in 15-cm containers during the summer in a glass-covered greenhouse in De Lier, The Netherlands. During the production of the plants, day temperatures ranged from 20° C. to 35° C., night temperatures ranged from 15° C. to 25° C. and minimum light levels were 135 watt/$m^2$. Plants were ten weeks old when the photograph was taken and about 20 weeks old when the detailed description was taken. In the following description, color references are made to The Royal Horticultural Society Colour Chart, Fifth Edition, except where general terms of ordinary dictionary significance are used.

Botanical classification: *Begonia* x *hiemalis* 'Dobegmotwohopi 33'.

Parentage:

*Female, or seed, parent*.—Proprietary breeding selection of *Begonia* x *hiemalis* identified as code number BG15-000801-003, not patented.

*Male, or pollen, parent*.—Proprietary breeding selection of *Begonia* x *hiemalis* identified as code number BG1463, not patented.

Propagation:

*Type*.—By vegetative tip cuttings.

*Time to initiate roots, summer*.—About 21 days at temperatures ranging from about 22° C. to 30° C.

*Time to initiate roots, winter*.—About 25 days at temperatures ranging from about 22° C. to 30° C.

*Time to produce a rooted young plant, summer*.—About 25 days at temperatures ranging from about 22° C. to 30° C.

*Time to produce a rooted young plant, winter*.—About 28 days at temperatures ranging from about 20° C. to 25° C.

*Root description*.—Medium in thickness, fibrous; whitish grey in color, actual color of the roots is dependent on substrate composition, water quality, fertilizer type and formulation, substrate temperature and physiological age of roots; plants of the new *Begonia* have not been observed to form tubers.

*Rooting habit*.—Moderately freely branching; medium density.

Plant description:

*Plant form and growth habit*.—Compact, upright and uniformly mounded plant habit; freely basal branching with about eight primary lateral branches each with about 16 secondary lateral branches; dense and bushy appearance; vigorous growth habit and moderate growth rate.

*Plant height, soil level to top of foliar plane*.—About 35 cm.

*Plant height, soil level to top of floral plane*.—About 40 cm.

*Plant width*.—About 35 cm.

*Lateral branch description*.—Length: About 12 cm. Diameter: About 1 cm. Internode length: About 3 cm. Texture and luster: Pubescent; semi-glossy. Aspect: Mostly upright. Strength: Moderately strong, flexible. Color, developing and developed: Close to 144B.

*Leaf description*.—Arrangement: Alternate, single. Length: About 12.3 cm. Width: About 9.2 cm. Shape: Broadly lanceolate, oblique. Apex: Acute. Base: Oblique with cordate tendencies. Margin: Serrate. Texture and luster, upper and lower surfaces: Smooth, glabrous; coriaceous; glossy. Venation pattern: Palmate; reticulate. Color: Developing leaves, upper surface: Close to 200A. Developing leaves, lower surface: Close to 185B. Fully expanded leaves, upper surface: Close to 147A; venation, close to 146D. Fully expanded leaves, lower surface: Close to 146D; venation, close to 146D. Petioles: Length: About 5 cm. Diameter: About 4.5 mm. Texture and luster, upper and lower surfaces: Smooth, glabrous; semi-glossy. Strength: Moderately strong; flexible. Color, upper and lower surfaces: Close to 144B.

Flower description:

*Flowering habit*.—Double-type flowers arranged in axillary cymes; freely flowering habit with typically about 17 flower buds and open flowers per inflorescence and about 160 flower buds and open flowers per plant at one time; flowers face mostly upright to outwardly.

*Fragrance*.—None detected.

*Natural flowering season*.—Plants begin flowering about 9 to 13 weeks after planting; long flowering period, in the garden plants flower freely and continuously from the late spring throughout the summer in Northern Europe and can be flowered year-round in greenhouses under short nyctoperiods.

*Flower longevity*.—Depending on temperature, individual flowers last about three to four weeks on the plant; flowers persistent.

*Inflorescence height*.—About 6 cm.

*Inflorescence diameter*.—About 15 cm.

*Flower buds*.—Length: About 1.9 cm. Diameter: About 2.3 cm. Shape: Spherical. Texture and luster: Smooth, glabrous; semi-glossy. Color: Close to 47A.

*Flower size*.—Diameter: About 4.8 cm by 5.5 cm. Depth: About 1.5 cm.

*Petals*.—Quantity per flower and arrangement: Typically four per flower arranged in a single whorl. Length: About 2.9 cm. Width: About 2.9 cm. Shape: Ovate. Apex: Obtuse. Base: Cuneate. Margin: Entire; not undulate. Texture and luster, upper and lower surfaces: Smooth, glabrous; semi-glossy. Color: When opening, upper surface: Close to 63A and N66A. When opening, lower surface: Close to 186A. Fully opened, upper surface: Close to 63A; venation, close to 63A; color becoming closer to 186A with subsequent development. Fully opened, lower surface: Close to 61C; venation, close to 182B; color becoming close to 176C with subsequent development.

*Petaloids*.—Quantity per flower and arrangement: Typically about 18 per flower arranged in about five to six whorl. Length: About 1.9 cm. Width: About 1.8 cm. Shape: Obovate. Apex: Obtuse and emarginate. Base: Cuneate. Margin: Entire; not undulate. Texture and luster, upper and lower surfaces: Smooth, glabrous; semi-glossy. Color: When opening, upper surface: Close to 63A and N66A. When opening, lower surface: Close to 186A. Fully opened, upper surface: Close to 63A; venation, close to 63A; color becoming closer to 186A with subsequent development. Fully opened, lower surface: Close to 61C; venation, close to 182B; color becoming close to 176C with subsequent development.

*Sepals*.—Quantity and arrangement: Typically two sepals arranged in a single whorl. Length: About 1 cm. Width: About 7 mm. Shape: Obovate. Apex: Rounded. Base: Cuneate and truncate. Margin: Entire. Texture and luster, upper and lower surfaces: Smooth, glabrous; semi-glossy. Color: When opening, upper surface: Close to 144A fading to close to 60C. When opening, lower surface: Close to 144A fading to close to 60A. Fully opened, upper surface: Close to 144A. Fully opened, lower surface: Close to 144A fading to close to 60B.

*Peduncles*.—Length: About 5 cm. Diameter: About 3.5 mm. Aspect: About 25° from the lateral branch axis. Strength: Moderately strong; flexible. Texture and luster: Smooth, glabrous; semi-glossy. Color: Close to 144B.

*Pedicels*.—Length: About 1.2 cm. Diameter: About 2 mm. Aspect: Mostly upright. Strength: Moderately strong; flexible. Texture and luster: Smooth, glabrous; semi-glossy. Color: Close to 174B.

*Reproductive organs*.—Stamens: To date, stamen development has not been observed on plants of the new *Begonia* as the stamens are transformed into petaloids. Pistils: Quantity per flower: About three. Pistil length: About 6 mm. Stigma diameter: About 6 mm. Stigma shape: Bilobed, spiral-shaped. Stigma color: Close to 14A. Style length: About 6 mm. Style color: Close to 14A. Ovary color: Close to 14A. Seeds: To date, seed development has not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate temperatures ranging from about 15° C. to about 30° C.

It is claimed:

1. A new and distinct *Begonia* plant named 'Dobegmotwohopi 33' as herein illustrated and described.

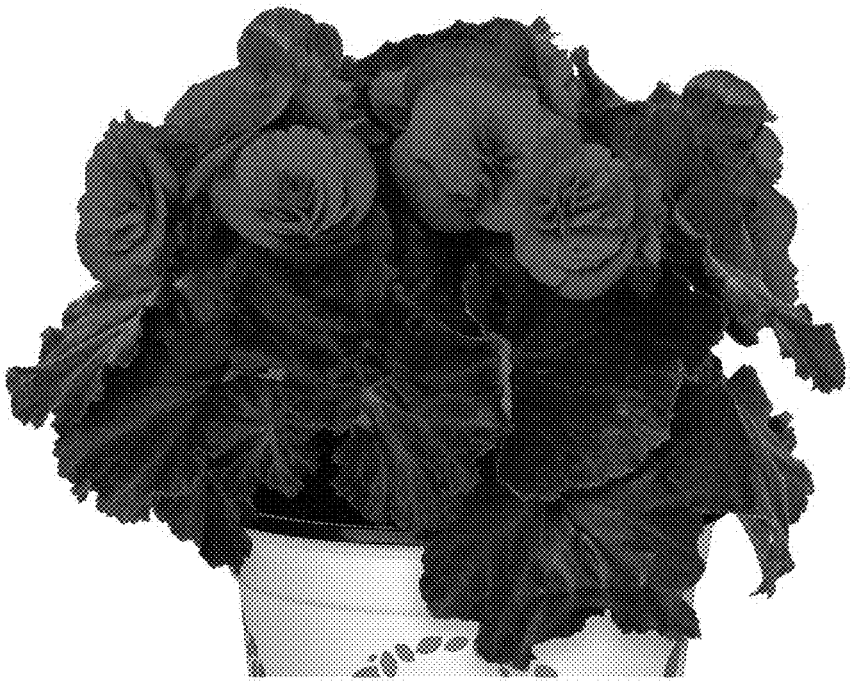

* * * * *